(12) United States Patent
Bitter et al.

(10) Patent No.: US 9,546,989 B2
(45) Date of Patent: Jan. 17, 2017

(54) METHOD FOR MEASURING THE CONCENTRATION OF A GAS COMPONENT IN A MEASUREMENT GAS

(71) Applicant: Siemens Aktiengesellschaft, Munich (DE)

(72) Inventors: Ralf Bitter, Karlsruhe (DE); Thomas Hankiewicz, Karlsruhe (DE); Christoph Wolfgang Marquardt, Karlsruhe (DE); Jan Nygren, Karlsruhe (DE); Kai-Uwe Pleban, Stutensee (DE); Franz Steinbacher, Karlsruhe (DE)

(73) Assignee: Siemens Aktiengesellschaft, Munich (DE)

( * ) Notice: Subject to any disclaimer, the term of this patent is extended or adjusted under 35 U.S.C. 154(b) by 288 days.

(21) Appl. No.: 14/503,650

(22) Filed: Oct. 1, 2014

(65) Prior Publication Data

US 2015/0089993 A1    Apr. 2, 2015

(30) Foreign Application Priority Data

Oct. 2, 2013 (EP) .................................... 13186991

(51) Int. Cl.
*G01J 3/28* (2006.01)
*G01N 33/00* (2006.01)
(Continued)

(52) U.S. Cl.
CPC ............. *G01N 33/0006* (2013.01); *G01J 3/28* (2013.01); *G01J 3/433* (2013.01);
(Continued)

(58) Field of Classification Search
CPC ...... G01J 2003/2869; G01J 3/28; G01J 3/433; G01N 21/3504; G01N 33/0006
(Continued)

(56) References Cited

U.S. PATENT DOCUMENTS 3,788,742 A * 1/1974 Garbuny ................ G01N 21/39
356/218
3,924,252 A * 12/1975 Duston ................ G08B 17/107
340/630

(Continued)

OTHER PUBLICATIONS

Kluczynski P et al., Theoretical description based on fourier analysis of wavelength-modulation spectrometry in terms of analytical and background signals, Applied Optics, vol. 38, No. 27 (1999).

(Continued)

*Primary Examiner* — Tri Ton
*Assistant Examiner* — Jarreas C Underwood
(74) *Attorney, Agent, or Firm* — Cozen O'Connor

(57) ABSTRACT

A method for measuring the concentration of a gas component in a measurement gas using a gas analyzer comprises varying the wavelength of the light of a wavelength-tunable light source within periodically consecutive scan intervals for wavelength-dependent scanning of a gas component absorption line of interest. The method also comprises modulating the wavelength of the light of the wavelength-tunable light source with a frequency, guiding the modulated light through the measurement gas onto a detector and demodulating a measurement signal generated by the detector in the event of a harmonic of the frequency. The method further comprises producing a measurement result by fitting a desired curve to the profile of the demodulated measurement signal. A function orthogonal to the desired curve is provided, and an orthogonal component of the measurement result is produced by fitting the orthogonal function to the profile of the demodulated measurement signal.

4 Claims, 3 Drawing Sheets

(51) Int. Cl.
  *G01J 3/433* (2006.01)
  *G01N 21/3504* (2014.01)
  *G01N 21/39* (2006.01)

(52) U.S. Cl.
  CPC .. *G01N 21/3504* (2013.01); *G01J 2003/2869* (2013.01); *G01N 33/00* (2013.01); *G01N 2021/399* (2013.01)

(58) Field of Classification Search
  USPC .................................................. 356/432–444
  See application file for complete search history.

(56) References Cited

U.S. PATENT DOCUMENTS

| | | | | |
|---|---|---|---|---|
| 3,995,960 A * | 12/1976 | Fletcher | ............. | G01N 21/1702 250/343 |
| 5,026,991 A * | 6/1991 | Goldstein | ............. | G01N 21/39 250/339.04 |
| 5,298,751 A * | 3/1994 | Fee | .................... | G01N 21/3518 250/338.5 |
| 5,317,156 A * | 5/1994 | Cooper | .................. | G01N 21/39 250/339.13 |
| 5,373,160 A * | 12/1994 | Taylor | .................... | G01N 21/39 250/338.5 |
| 7,107,048 B2 * | 9/2006 | Chandler | ................ | G06F 17/17 455/423 |
| 7,251,034 B2 * | 7/2007 | Kluczynski | ........... | G01J 3/4338 356/437 |
| 7,969,576 B1 * | 6/2011 | Buckley | ................ | G01N 21/39 356/437 |
| 8,044,353 B2 * | 10/2011 | Bitter | ..................... | G01N 21/37 250/338.1 |
| 8,158,945 B2 * | 4/2012 | Bitter | ................. | G01N 21/3504 250/339.13 |

OTHER PUBLICATIONS

Kluczynski P et al., Characterization of background signals in wavelength-modulation spectrometry in terms of a Fourier based theoretical formalism, Applied Optics, vol. 40, No. 6 (2001).

* cited by examiner

METHOD FOR MEASURING THE CONCENTRATION OF A GAS COMPONENT IN A MEASUREMENT GAS

FIELD OF INVENTION

The invention relates to a method for measuring the concentration of a gas component in a measurement gas using a gas analyzer. The wavelength of the light of a wavelength-tunable light source in the gas analyzer is varied within periodically consecutive scan intervals for the purpose of wavelength dependent scanning of a gas component absorption line of interest. The wavelength of the light of the wavelength-tunable light source is additionally modulated in the process with a frequency, wherein the modulated light is guided through the measurement gas onto a detector. A measurement signal generated by the detector is demodulated in the event of a harmonic of the frequency, and a measurement result is produced by fitting a desired curve to the profile of the demodulated measurement signal.

DESCRIPTION OF THE RELATED ART

In a known method (described in, e.g., EP 1 475 618 B1), a wavelength-tunable light source in the form of a laser diode generates light in the infrared region which is led through a process gas to be measured (measurement gas) and subsequently detected. The wavelength of the light is tuned to a specific absorption line of the gas component respectively to be measured by periodically scanning the absorption line as a function of the wavelength. For this purpose, the laser diode is driven by a ramp current signal or triangular current signal within periodically consecutive scan intervals.

During the comparatively slow scanning of the absorption line, the wavelength of the generated light with high frequency and low amplitude is further modulated sinusoidally. Since the profile of the absorption line is nonlinear, harmonics above the modulation frequency are also generated in the measurement signal obtained in the detection. The measurement signal is usually demodulated at an $n^{th}$ harmonic, and preferably the second harmonic, by phase-sensitive lock-in technology, and evaluated for each scan interval to yield a measurement result.

Given a low modulation amplitude, the detection of the $n^{th}$ harmonic is directly proportional to the $n^{th}$ derivative of the direct measurement signal. The evaluation is performed, for example, by fitting (curve fitting) of the profile, to be expected in the ideal case, of the demodulated measurement signal (desired curve) to the actual profile (actual curve) thereof. Finally, the concentration of the gas component to be measured is determined from the measurement result obtained in the process.

Temperature changes within the gas analyzer can lead to changes in the measurement results. This characteristic of the gas analyzer, which is termed drift, substantially limits its measurement response and applications which are to be realized. One cause of the drift can, inter alia, be etalons in the optical beam path. The etalons lead in the profile of the demodulated measurement signal to periodic structures which lie in the frequency range of the absorption signal to be expected. In the curve fitting, this leads to poorly fitted functions and deviations between the determined concentrations and the actual concentrations of the gas component to be measured.

In order to suppress said interference signal components, it is known from the above-mentioned EP 1 475 618 B1 to lead a portion of the light generated by the light source directly to a monitor detector, and to demodulate and evaluate the monitor signal obtained at the $n^{th}$ harmonic. Each deviation of the demodulated monitor signal from a zero line is based on an optical interference which, should it lie in the region of the light source or in the path segment of the beam path which is used jointly by the measurement channel and monitor channel, also impairs the measurement signal. The interference is compensated by a predistortion of the drive of the light source by additionally modulating the wavelength of the light with the $n^{th}$ harmonic, the modulation intensity being dependent on the demodulated monitor signal.

The decoupling of a portion of the generated light onto the monitor detector is, however, associated with increased outlay in terms of construction and circuitry which goes hand in hand with a higher interference sensitivity. Moreover, it is impossible to compensate interference occurring in the measurement signal outside the common sections of the measurement and monitor channel.

It is known from EP 2 336 738 A1 or EP 1 927 831 A1 to vary the optical path length, for example, by mechanical vibration of the light source, and to average out the disturbing periodic structures from the demodulated measurement signal. However, it is possible thereby to reduce only specific interference produced by parallel optical surfaces in the beam path.

SUMMARY OF THE RELATED ART

It is an object of the invention to reduce in the measurement results changes resulting in the gas analyzer from interfering influences such as temperature changes.

In accordance with the invention, the object is achieved by providing a function orthogonal to the desired curve, and producing an orthogonal component of the measurement result by fitting the orthogonal function to the profile of the demodulated measurement signal. For the purpose of measurement calibration given a known concentration of the gas component to be measured, an interfering parameter is varied and there is determined in the process an error which consists of an inphase component, in the form of the difference between the obtained measurement result and a desired measurement result, and of the orthogonal component.

A relationship between the inphase component of the error and its orthogonal component is further determined. In the case of the measurement of an unknown concentration of the gas component, the measurement result obtained in the process is corrected with an inphase component which is determined, with the aid of the relationship determined in the measurement calibration, from the likewise obtained orthogonal component.

The function orthogonal to the desired curve, i.e., to the profile of the demodulated measurement signal to be expected in the ideal case, does not, owing to its orthogonal characteristic, correlate with the form of the absorption line to be measured (more precisely the profile of its demodulation frequency component). Instead of this, the orthogonal function correlates with the orthogonal components of interference signals whose inphase components appear, for their part, directly as interference signal components in the measurement signal.

Given that the function orthogonal to a desired curve in addition to the desired curve, the orthogonal function is also fitted to the demodulated measurement signal, there is also obtained an orthogonal component of the measurement result which is equal to the orthogonal component of the interference besides the disturbed measurement result (more precisely the disturbed inphase component of the measurement result). It is, therefore, possible in the course of a measurement calibration in the case when the concentration of the gas component to be measured is known to determine a measuring error with an inphase component and an orthogonal component, the inphase component of the error consisting of the difference between the measurement result obtained and a desired measurement result of the known concentration.

Consequently, after determination of a relationship between the inphase component and the orthogonal component of the error it is possible, when measuring an unknown concentration of the gas component, to correct the measurement result obtained in this case by using said relationship and the orthogonal component likewise obtained.

As already mentioned above, the interference and/or the error can be largely dependent on temperature. Consequently, it is possible to vary the operating temperature of the gas analyzer during the calibration so that the determined error is dependent on temperature and/or changes in the course of the warming or cooling of the gas analyzer. The result of etalon effects in the optical beam path is that the error changes periodically over the temperature profile, i.e., the vector formed by the inphase component and the orthogonal component of the error rotates.

Other interfering effects such as, the change in the reflectivity of an etalon, lead, in contrast, to changes in length of the error vector and/or offsets of the inphase component and orthogonal component. It is, therefore, possible to distinguish between different types of interference on the basis of the error profile, i.e., the way in which the error varies.

Since, as already mentioned, etalon effects lead to a periodic change or fluctuation in the error over the temperature profile, such that the error vector rotates, the relationship to be determined between the inphase component and the orthogonal component of the error is not unique. Consequently, it is preferred, during the measurement calibration, also to measure the temperature in order to be able to determine a functional, and thus unique, relationship between the inphase component of the error, its orthogonal component and the measured temperature.

Alternatively or in addition, it is possible also to compensate the influence of error of an interfering gas component in the measurement gas, which component is superposed spectrally on the absorption line of interest of the gas component to be measured. In this case, the gas analyzer is calibrated for different known concentrations of the interfering gas component, and in the process a functional relationship is determined between the inphase component of the error, its orthogonal component and the concentration of the interfering gas component.

Although it would be possible to determine the interfering gas component in the same way as the gas component to be measured by fitting an appropriate desired curve to the profile of the demodulated measurement signal, the effect of this would be to inversely render the gas component to be measured disturbingly noticeable. By contrast, the method according to the invention has the advantage that the gas component of interest exerts no influence on the interfering gas measurement. Furthermore, the interfering gas measurement is limited to the component of spectral and frequency relevance, and this prevents the interfering gas measurement from being influenced by further influencing parameters such as, for example, a third gas component which is superposed spectrally only by the interfering gas component, but not by the gas component to be measured.

BRIEF DESCRIPTION OF THE DRAWINGS

Reference is made below to the figures of the drawing for the purpose of further explanation of the invention as follows.

DETAILED DESCRIPTION OF THE PRESENTLY PREFERRED EMBODIMENTS

Figure 1:
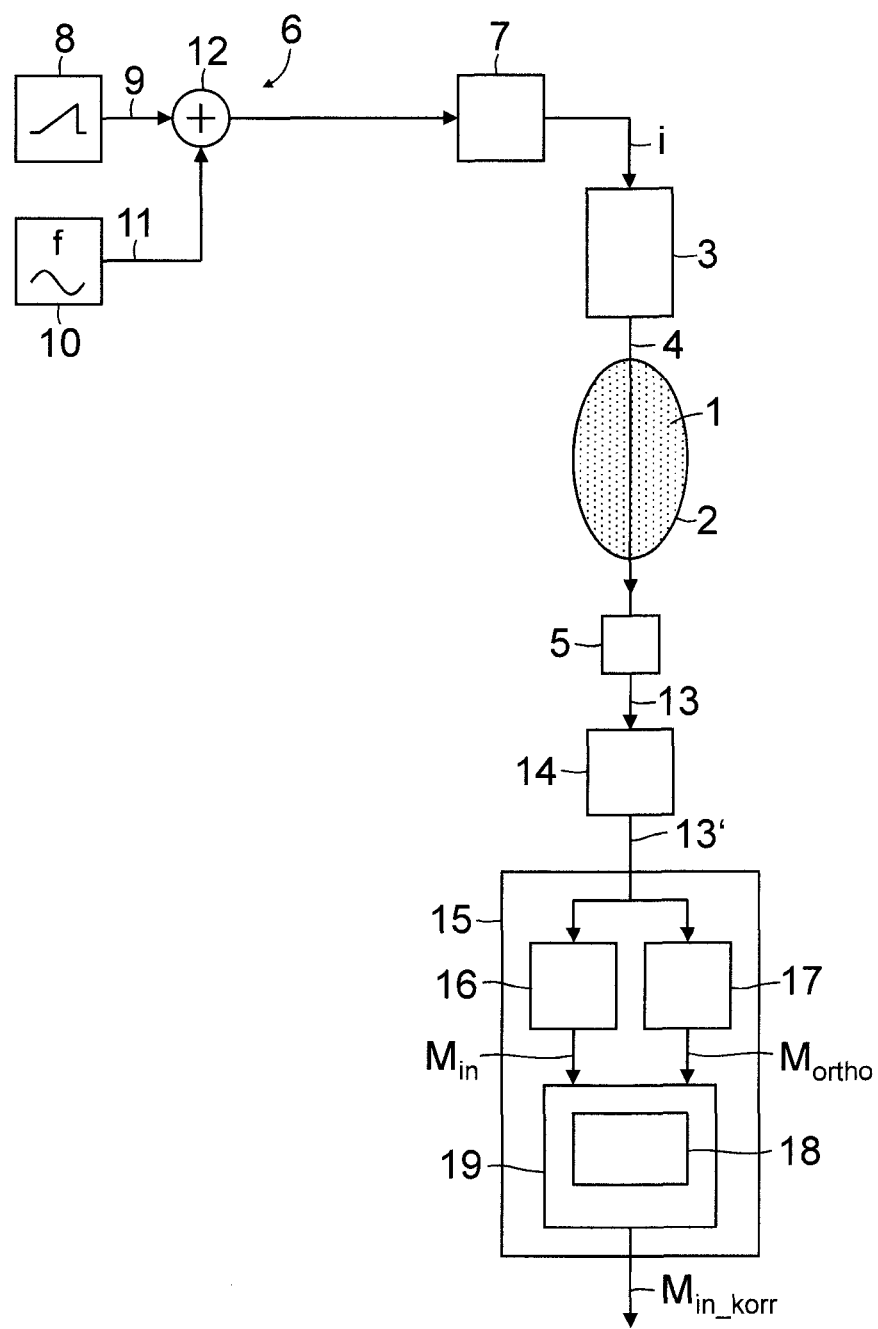
FIG. 1 shows a gas analyzer for carrying out the method of the invention in accordance with one embodiment of the present invention.

The gas analyzer shown in the form of a simplified block diagram in FIG. 1 is a laser spectrometer for measuring the concentration of at least one gas component of interest in a measurement gas 1 which is contained in a measuring volume 2, such as a sample cell or a process gas line. The spectrometer includes a light source 3 in the form of a laser diode whose light 4 falls on a measuring detector 5 after traversing the measurement gas 1.

A current source 7 controlled by a modulation device 6 feeds the laser diode 3 with an injection current i, the intensity and wavelength of the generated light 4 depending on the current i and the operating temperature of the laser diode 3. The modulation device 6 comprises a first signal generator 8 which drives the current source 7 periodically with the aid of a prescribed function 9, such as, preferably, a ramp function or a triangular function 9, in order to scan a selected absorption line of the gas component of interest with the aid of the wavelength of the generated light 4, which follows the profile of the current i more or less linearly. A second signal generator 10 generates a sinusoidal signal 11 of higher frequency $f_0$, which is used to modulate the ramp function or triangular function 9 in an adding element 12.

The measuring detector 5 generates a measurement signal 13 as a function of the detected light intensity, which measurement signal is demodulated in a lock-in amplifier 14 at a harmonic $nf_0$ (n=1, 2, 3 . . . ), here $2f_0$ for example, of the modulation frequency $f_0$. In a downstream evaluation device 15, the demodulated measurement signal 13' for each scan interval is evaluated to form a measurement result. For this purpose, a desired curve corresponding to the ideal demodulated measurement signal 13' is fitted to the demodulated measurement signal 13' in a first arithmetic logic unit 16, and a function orthogonal to the desired curve is fitted to the demodulated measurement signal 13' in a second arithmetic logic unit 17.

As already explained at the beginning, temperature changes within the gas analyzer can lead to drifting of the measurement results, and the cause of the drift is etalons in the optical beam path that lead to periodic structures in the profile of the demodulated measurement signal 13'.

Figure 2:
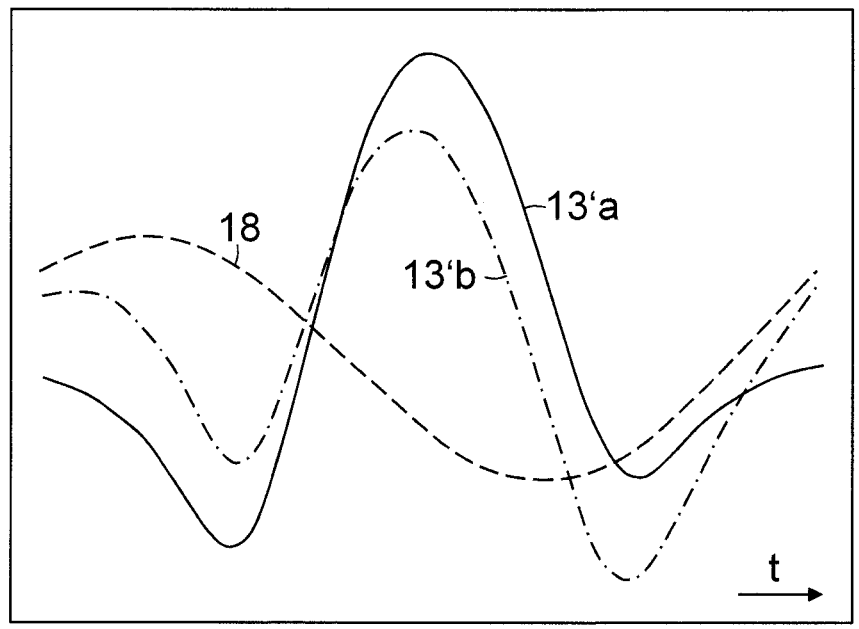
FIG. 2 shows an example of the interference of a demodulated measurement signal in accordance with one embodiment of the present invention.

By way of example, FIG. 2 shows an interference-free measurement signal 13'a demodulated at the second harmonic $2f_0$ of the modulation frequency $f_0$, a periodic interference 18, and the measurement signal 13'b, on which the interference 18 is superposed. It can be seen at once that fitting a desired curve (19 in FIG. 3) corresponding to the ideal demodulated measurement signal 13'a to the disturbed measurement signal 13'b does not lead to a correct determination of concentration.

Figure 3:
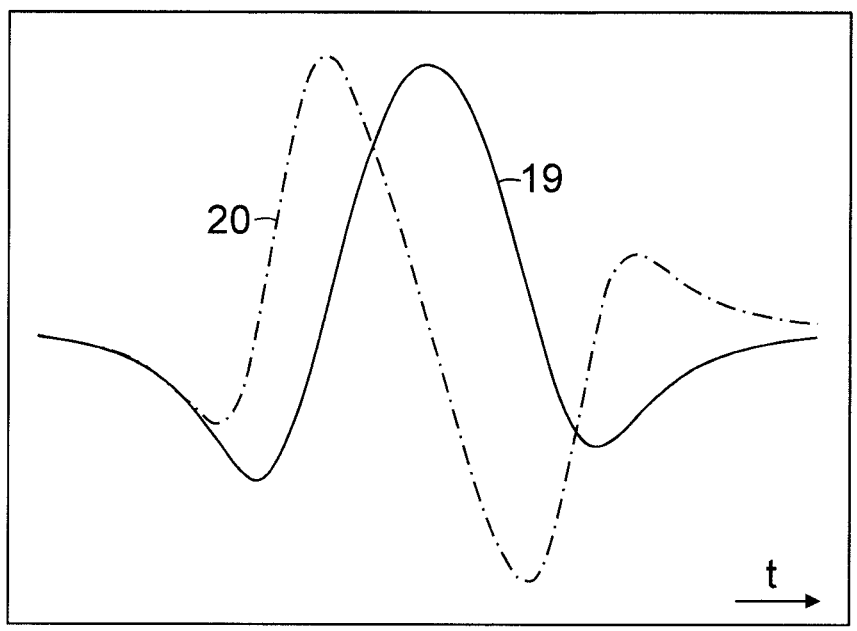
FIG. 3 shows an example of a desired curve corresponding to the profile of the demodulated measurement signal ideally to be expected, and a function orthogonal to the desired curve in accordance with one embodiment of the present invention.

By way of example, FIG. 3 shows the desired curve 19 corresponding to the profile of the demodulated measurement signal 13' ideally to be expected and a function 20 orthogonal thereto. In contrast to the desired curve 19, the orthogonal function 20 correlates not with the demodulated measurement signal 13' or 13'a, but with the orthogonal components of interference signals whose inphase components for their part appear directly as interference signal components in the demodulated measurement signal 13' or 13'a.

Returning to FIG. 1, the arithmetic logic unit 16 supplies a more or less disturbed measurement result M, more precisely an inphase component $M_{in}$ of the measurement result M comprising a useful component $S=S_{in}$ and an inphase interference component $N_{in}$. The arithmetic logic unit 17 produces an orthogonal component $M_{ortho}$ of the measurement result M consisting of the orthogonal interference component $N_{ortho}$: $M=M_{in}+M_{ortho}=(S+N_{in})+N_{ortho}$, where $S=S_{in}$ and $S_{ortho}=0$.

Figure 4:
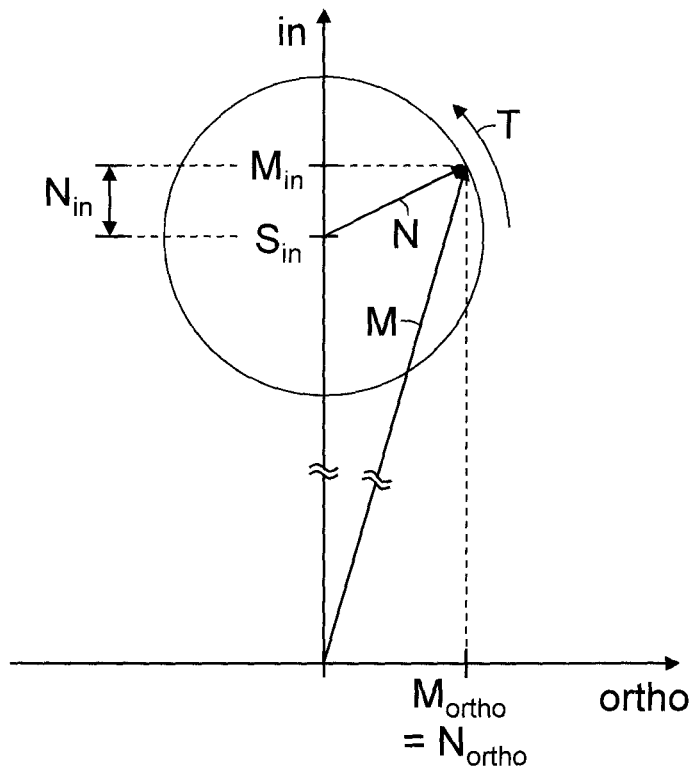
FIG. 4 shows an example of a temperature-dependent measurement result obtained by fitting the desired curve and the orthogonal function to the demodulated measurement signal in accordance with one embodiment of the present invention.

By way of example, FIG. 4 shows a phasor diagram of the measurement result M with its inphase and orthogonal components. For the purpose of measurement calibration given a known concentration of the gas component to be measured, the operating temperature of the gas analyzer is varied and there is determined in the process an error N which comprises the inphase component $N_{in}$, in the form of the difference between the inphase measurement result $M_{in}$ and the desired measurement result $S_{in}$, and of the orthogonal component $M_{ortho}$.

In a next step, a relationship between the inphase component $N_{in}$ of the error N and its orthogonal component $N_{ortho}$ is determined. FIG. 4 shows a simple case in which the error N based on etalon effects describes over the temperature T an approximate circle about the desired measurement result $S_{in}$. The relationship is stored in a memory 18 (FIG. 1) of a further arithmetic logic unit 19, downstream of the arithmetic logic units 16, 17, which, in the course of the measurement of an unknown concentration of the gas component, corrects the inphase measurement result $M_{in}$ obtained in the process with the aid of an inphase component which is determined by using the stored relationship from the orthogonal component $M_{ortho}$ likewise obtained. In the simple example shown in FIG. 4, the radius $R=|N|$ of the circle is determined during the measurement calibration, and when an unknown concentration of the gas component is being measured the inphase measurement result $M_{in}$ obtained in the process is corrected as follows: $M_{in\_korr}=M_{in}\pm(R^2-M^2_{ortho})^{1/2}$.

Figure 5:
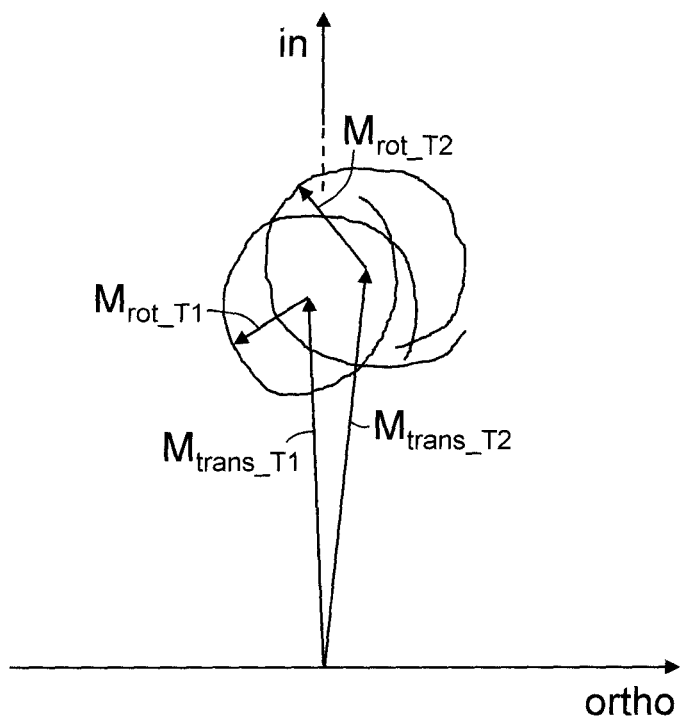
FIG. 5 shows an example of changes in the measurement result within different temperature ranges in accordance with one embodiment of the present invention.

FIG. 5 shows an example of changes in the measurement result M within different temperature ranges T1 and T2, for example T1=45° C. to 49° C. and T2=−6° C. to −2° C. In reality, in some circumstances a plurality of etalons with various dependencies and sensitivities concerning temperature are active during measurement, and so the errors they cause can rotate in the phasor diagram at different speeds.

Furthermore, the amplitudes (phasor lengths) can change because of changes in intensity (alignment dependence of the temperature) or through changes in reflectivities (for example coatings of optical surfaces). The amplitudes also change whenever other interfering influences are added which do not behave like etalons. The measurement results M(T1), M(T2) then comprises components $M_{trans\_T1}$, $M_{trans\_T2}$ which move by translation in the phasor diagram as a function of the temperature, and components, $M_{rot\_T1}$, $M_{rot\_T2}$ which move by rotation.

Although the present invention has been described above with reference to presently preferred embodiments, it is not limited thereto but rather can be modified in a wide variety of ways. In particular, the invention can be altered or modified in multifarious ways without departing from the essence of the invention.

What is claimed is:

1. A method for measuring the concentration of a gas component in a measurement gas using a gas analyzer, the method comprising:

varying the wavelength of the light of a wavelength-tunable light source within periodically consecutive scan intervals for wavelength-dependent scanning of a gas component absorption line of interest;

modulating the wavelength of the light of the wavelength-tunable light source with a frequency;

guiding the modulated light through the measurement gas onto a detector;

demodulating a measurement signal generated by the detector in the event of a harmonic of the frequency; and producing a measurement result by fitting a desired curve to the profile of the demodulated measurement signal, wherein a function orthogonal to the desired curve is provided, and an orthogonal component of the measurement result is produced by fitting the orthogonal function to the profile of the demodulated measurement signal, wherein, given a known concentration of the gas component to be measured, an interfering parameter is varied and it is determined in the process an error, which comprises an inphase component ($N_{in}$), in the form of the difference between the obtained measurement result and a desired measurement result, and the orthogonal component, wherein a relationship between the inphase component of the error and its orthogonal component is further determined, and wherein, in the case of the measurement of an unknown concentration of the gas component, the measurement result obtained in the process is corrected with an inphase component which is determined, with the aid of the relationship determined in the measurement calibration, from the likewise obtained orthogonal component.

2. The method of claim 1, wherein the relationship determined in the measurement calibration is determined in the form of a functional relationship between the inphase component of the error, its orthogonal component and the measured or known interfering parameter.

3. The method of claim 1, wherein the operating temperature of the gas analyzer is varied as interfering parameter.

4. The method of claim 1, wherein the concentration of an interfering gas component in the measurement gas used for the calibration is varied as interfering parameter.

\* \* \* \* \*